（12）United States Patent
Maki et al.

(10) Patent No.: US 11,786,701 B2
(45) Date of Patent: Oct. 17, 2023

(54) MEDICAL DEVICE DRIVE APPARATUS AND FORCE INFORMATION CALCULATION METHOD

(71) Applicant: TERUMO KABUSHIKI KAISHA, Tokyo (JP)

(72) Inventors: Shin Maki, Ebina (JP); Tomoki Utsugida, Machida (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 747 days.

(21) Appl. No.: 16/704,338

(22) Filed: Dec. 5, 2019

(65) Prior Publication Data

US 2020/0108226 A1  Apr. 9, 2020

Related U.S. Application Data

(63) Continuation of application No. PCT/JP2018/020144, filed on May 25, 2018.

(30) Foreign Application Priority Data

Jun. 5, 2017  (JP) ................... 2017-111098

(51) Int. Cl.
*A61M 25/09*   (2006.01)
*A61M 25/01*   (2006.01)
*A61M 25/10*   (2013.01)

(52) U.S. Cl.
CPC ... *A61M 25/0113* (2013.01); *A61M 25/09041* (2013.01); *A61M 2025/1079* (2013.01); *A61M 2205/3327* (2013.01)

(58) Field of Classification Search
CPC ......... A61M 25/0113; A61M 25/09041; A61B 34/20; A61B 34/35
See application file for complete search history.

(56) References Cited

U.S. PATENT DOCUMENTS 5,279,559 A  *  1/1994  Barr .................. A61M 25/0158
604/95.05
2001/0022831 A1  9/2001  Meek et al.
(Continued)

FOREIGN PATENT DOCUMENTS

JP   2002355730 A   12/2002
JP   2003177186 A   6/2003
(Continued)

OTHER PUBLICATIONS

International Search Report (PCT/ISA/210) dated Aug. 21, 2018, by the Japan Patent Office as the International Searching Authority for International Application No. PCT/JP2018/020144.
(Continued)

*Primary Examiner* — Courtney B Fredrickson
(74) *Attorney, Agent, or Firm* — BUCHANAN INGERSOLL & ROONEY PC

(57) ABSTRACT

A medical device drive apparatus for inserting an elongated medical device into a blood vessel includes a sub-drive unit that enables fine movement of the elongated medical device and a main drive unit that enables long distance movement of the elongated medical device, in which the sub-drive unit includes a sub-drive unit body and a sub-movable portion movable with respect to the sub-drive unit body, and information on minute force applied to the elongated medical device is calculated based on information on acceleration of the sub-movable portion.

20 Claims, 13 Drawing Sheets

(56) References Cited

U.S. PATENT DOCUMENTS

| | | | |
|---|---|---|---|
| 2008/0009791 A1* | 1/2008 | Cohen | A61M 25/0105 |
| | | | 604/95.01 |
| 2011/0178508 A1 | 7/2011 | Ullrich | |
| 2012/0035467 A1* | 2/2012 | Lichtenstein | A61B 5/062 |
| | | | 600/424 |
| 2013/0190726 A1 | 7/2013 | Kesner et al. | |
| 2015/0001968 A1 | 1/2015 | Zirps | |
| 2017/0056032 A1* | 3/2017 | Look | A61M 1/74 |

FOREIGN PATENT DOCUMENTS

| | | | |
|---|---|---|---|
| JP | 2010182084 A | 8/2010 |
| JP | 2013517065 A | 5/2013 |
| JP | 2013517866 A | 5/2013 |

OTHER PUBLICATIONS

Written Opinion (PCT/ISA/237) dated Aug. 21, 2018, by the Japan Patent Office as the International Searching Authority for International Application No. PCT/JP2018/020144.

\* cited by examiner

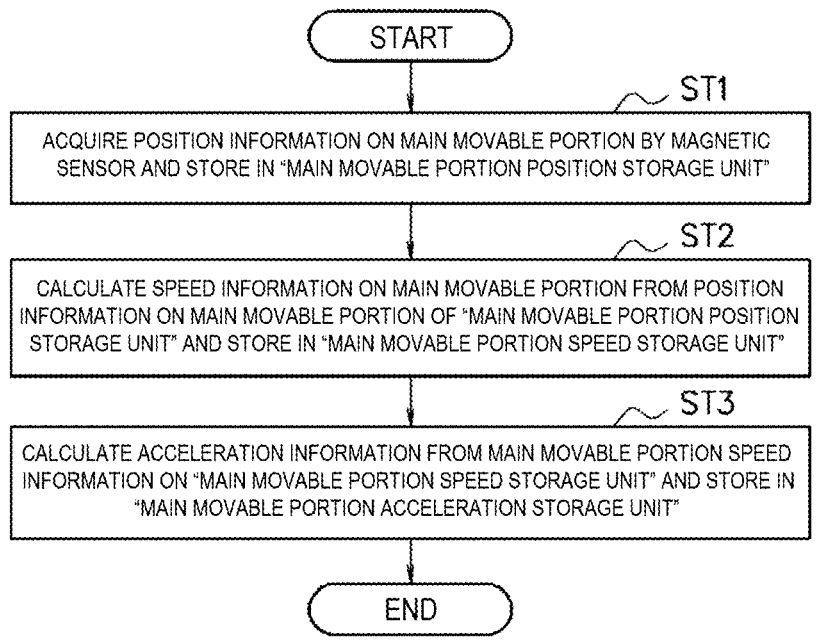

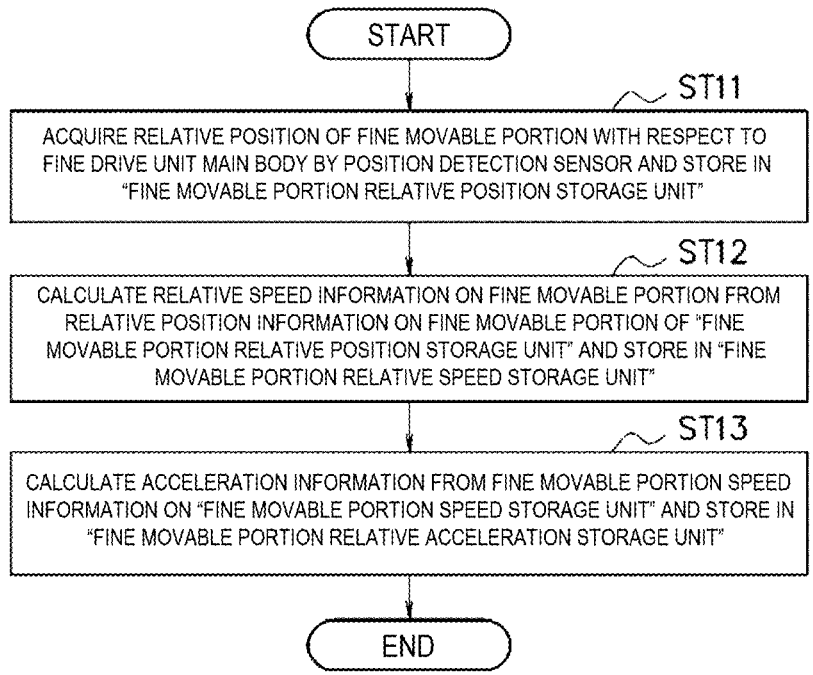

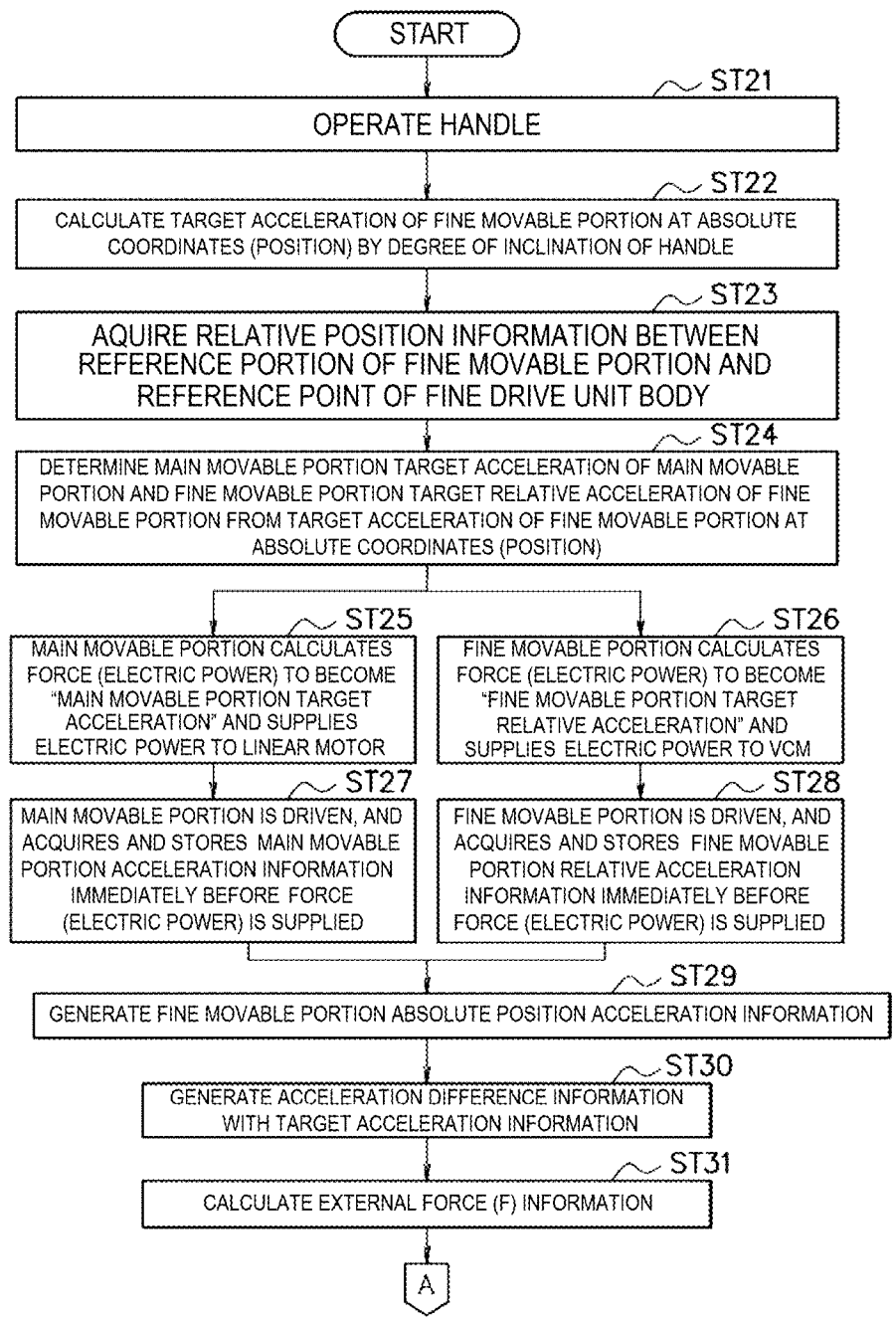

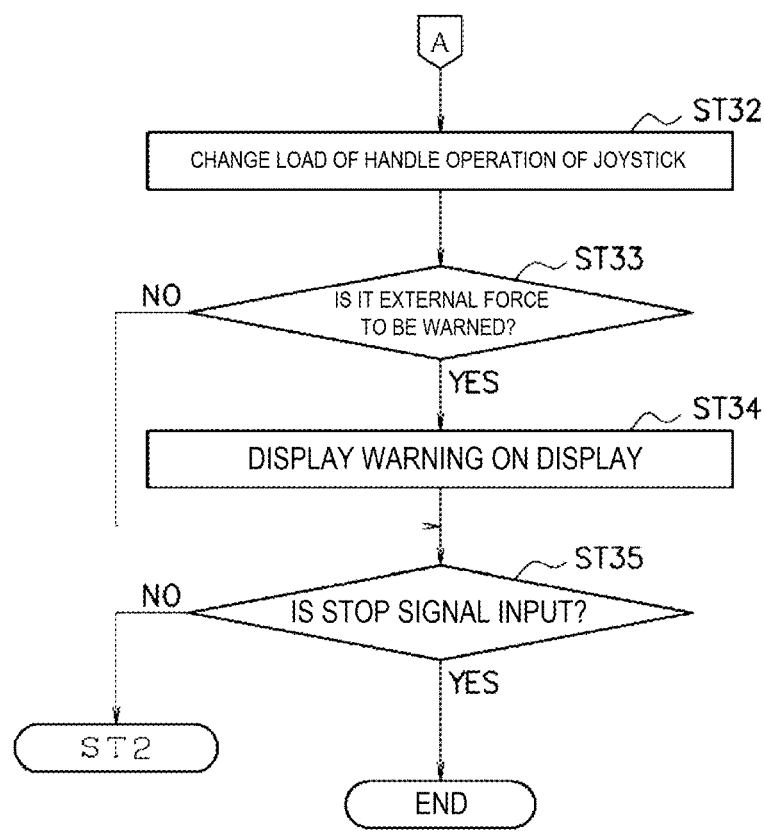

MEDICAL DEVICE DRIVE APPARATUS AND FORCE INFORMATION CALCULATION METHOD

CROSS-REFERENCES TO RELATED APPLICATIONS

This application is a continuation of International Application No. PCT/JP2018/020144 filed on May 25, 2018, which claims priority to Japanese Application No. 2017-111098 filed on Jun. 5, 2017, the entire content of both of which is incorporated herein by reference.

FIELD OF THE DISCLOSURE

The present disclosure generally relates to a medical device drive apparatus and a force information calculation method for remote operation of a medical device such as a guide wire used for a catheter and the like inserted into a blood vessel of a living body.

BACKGROUND DISCUSSION

Intravascular treatment is performed in which a catheter or the like is inserted into a blood vessel of a patient to treat, for example, a stenosed site in the blood vessel.

In the intravascular treatment, in order to insert the catheter, a doctor generally needs to operate a guide wire inserted in the blood vessel in order to guide the catheter.

In order to operate the guide wire, it is necessary for a doctor to perform the treatment while seeing the inserted state of the guide wire through an X-ray and visually confirming the inserted state of the guide wire in an image.

However, since this treatment method needs to be performed in a vicinity of a patient, there is a risk that a doctor may be exposed by X-rays.

Therefore, a proposal has been made that a doctor inserts, for example, a guide wire using a robot that can be remotely operated instead of directly on the patient (for example, U.S. Patent Publication No. 2015-1968).

However, when a remotely operatable robot is used, it can be difficult for a doctor to acquire information on slight force when directly operating by hand. For this reason, for example, even if a distal end of the guide wire attaches to a lesion area in an intravascular wall and the distal end of the guide wire cannot advance, it may not be possible to grasp the occurrence of the situation.

By continuing to advance the guide wire without noticing the situation, there may be a risk that the guide wire will be bent and eventually suddenly jump and break through the blood vessel wall.

SUMMARY

In accordance with an exemplary embodiment, a medical device drive apparatus and a force information calculation method are disclosed capable of accurately detecting minute changes in force generated in a blood vessel.

According to a first aspect of the present disclosure, a medical device drive apparatus for inserting an elongated medical device into a blood vessel includes a main drive unit that enables movement of the elongated medical device, a sub-drive unit that enables movement of the elongated medical device at a shorter distance than the main drive unit, and includes a sub-drive unit body and a sub-movable portion movable with respect to the sub-drive unit body and a sensor for acquiring information on acceleration of the sub-movable portion, in which information on force applied to the elongated medical device is calculated based on the information on acceleration of the sub-movable portion.

In accordance with an aspect, a relatively slight (or relatively minute) force can be detected from the blood vessel with the acceleration information on the movement of the sub-movable portion, a change in force generated in the blood vessel or the like can be detected with relatively high accuracy.

When performing a long distance movement such as moving an elongated medical device such as a guide wire to the vicinity of a target portion in the blood vessel, it can be moved by the main drive unit, so that the elongated medical device can be moved relatively efficiently.

In accordance with an exemplary embodiment, for example, after being moved by the main drive unit, since it is possible to detect a slight change in the force applied to the medical device in the blood vessel with the acceleration information on the movement of the sub-movable portion with respect to the sub-drive unit body, conflicting demands for efficient movement of a medical device and detection of slight (or relatively minute) force change can be achieved at the same time.

In accordance with an exemplary embodiment, for example, as the main drive unit takes charge of detection of a relatively large force to move the elongated medical device over a long distance and the sub-drive unit can take charge of detection of information on the minute force applied to the elongated medical device which can be difficult to detect with the main drive unit, the above-described conflicting demands can be achieved at the same time.

In accordance with an exemplary embodiment, since it is possible to detect relatively slight (relatively minute) force from the blood vessel with the information on change in the movement speed of the sub-movable portion, a change in force generated in the blood vessel can be detected with relative high accuracy, for example, without providing a special sensor such as a "force sensor".

Furthermore, since a special disposal of a "force sensor" is unnecessary, the cost can be reduced at the same time.

In accordance with an exemplary embodiment, the medical device drive apparatus as one embodiment of the present disclosure may further include an input unit that enables to input target acceleration information on the elongated medical device, in which target acceleration information on the sub-movable portion may be obtained based on the target acceleration information on the elongated medical device input to the input unit, and the information on the force applied to the elongated medical device may be calculated from a difference between the target acceleration information on the sub-movable portion and actual acceleration information on the sub-movable portion.

In accordance with an exemplary embodiment, the information on the force applied to the elongated medical device is calculated from the difference between the target acceleration information such as the information on acceleration of the sub-movable portion and the acceleration information such as the actual acceleration information on the sub-movable portion, for example, it is possible to detect the information on the force applied to the elongated medical device with relatively high accuracy without using a special sensor or the like such as a force sensor.

In the medical device drive apparatus as one embodiment of the present disclosure, the main drive unit may include a main drive unit body and a main movable portion movable with respect to the main drive unit body, and the sub-drive unit body may move with the movement of the main movable portion.

In accordance with an exemplary embodiment, by moving the main movable portion, the sub-drive unit body is moved and the medical device is also moved, so that the sub-drive unit body can be moved relatively efficiently.

In the medical device drive apparatus as one embodiment of the present disclosure, the sensor may include a first sensor for acquiring information on acceleration of the main movable portion and a second sensor for acquiring information on relative acceleration of the sub-movable portion with respect to the sub-drive unit body, and the information on acceleration of the sub-movable portion may be calculated based on the information on acceleration of the main movable portion and the information on relative acceleration of the sub-movable portion.

In accordance with an exemplary embodiment, since the information on acceleration of the sub-movable portion is calculated based on the information on acceleration of the main movable portion and the information on relative acceleration of the sub-movable portion, the information on acceleration of the sub-movable portion can be acquired without disposing a special position sensor with respect to the sub-movable portion and acquiring the information on an absolute position of the sub-movable portion, and thereby, the cost can be reduced.

In the medical device drive apparatus as one embodiment of the present disclosure, the first sensor may be a first position sensor for acquiring information on absolute position of the main movable portion, the second sensor may be a second position sensor for acquiring information on relative position of the sub-movable portion with respect to the sub-drive unit body, the information on acceleration of the main movable portion may be calculated from the information on absolute position of the main movable portion, and the information on relative acceleration of the sub-movable portion may be calculated from the information on relative position of the sub-movable portion.

The medical device drive apparatus as one embodiment of the present disclosure may further include an input unit that enables to input target acceleration information on the elongated medical device, in which target acceleration information on the sub-movable portion may be calculated based on the target acceleration information on the elongated medical device input to the input unit, and target acceleration information on the main movable portion and target relative acceleration information on the sub-movable portion with respect to the sub-drive unit body may be determined based on the target acceleration information on the sub-movable portion.

In accordance with exemplary embodiment, since the target acceleration information on the main movable portion and the target relative acceleration information on the sub-movable portion with respect to the sub-drive unit body is determined based on the target acceleration information on the sub-movable portion, it is possible to control each of the sub-movable portion and the main movable portion individually.

In the medical device drive apparatus as one embodiment of the present disclosure, in the determination of the target acceleration information, the target acceleration information on the main movable portion and the target relative acceleration information on the sub-movable portion may be determined so that a relative position of the sub-movable portion with respect to the sub-drive unit body is within a predetermined range.

In accordance with an exemplary embodiment, since the target acceleration information on the main movable portion and the target relative acceleration information on the sub-movable portion are determined so that a relative position of the sub-movable portion with respect to the sub-drive unit body is within a predetermined range, a slight change in the force applied to the medical device in the blood vessel can be detected with high accuracy.

In the medical device drive apparatus as one embodiment of the present disclosure, the information on the force applied to the elongated medical device may be calculated based on a difference between the target relative acceleration information on the sub-movable portion and the information on relative acceleration of the sub-movable portion, and a difference between the target acceleration information on the main movable portion and the information on acceleration of the main movable portion.

In accordance with an exemplary embodiment, the medical device drive apparatus as one embodiment of the present disclosure may further include an operation unit for inputting the target acceleration information on the elongated medical device to the input unit, in which the calculated information on the force applied to the elongated medical device may be reflected on the operation unit.

In accordance with an exemplary embodiment, since an operator who operates the operation unit can feel the force applied to the elongated medical device from the blood vessel, the apparatus can be relatively easy to operate.

In the medical device drive apparatus as one embodiment of the present disclosure, a notification may be given when the calculated information on the force applied to the elongated medical device exceeds a predetermined value.

In accordance with an exemplary embodiment, since the operator of the medical device drive apparatus can know the presence or absence of an abnormality, the apparatus becomes more reliable.

In the medical device drive apparatus as one embodiment of the present disclosure, movement of the sub-movable portion may be stopped when the calculated information on the force applied to the elongated medical device exceeds a predetermined value.

In accordance with an exemplary embodiment, since the movement of the sub-movable portion is stopped when the information on the force applied to the elongated medical device exceeds a predetermined value, the apparatus becomes relatively safer and more reliable.

In accordance with a second aspect of the present disclosure, a medical device drive apparatus is disclosed for inserting an elongated medical device into a blood vessel comprising: a main drive unit configured to enable movement of the elongated medical device; a sub-drive unit configured to enable movement of the elongated medical device, the sub-drive unit including a sub-drive unit body and a sub-movable portion movable with respect to the sub-drive unit body; a sensor configured to acquire information on acceleration of the sub-movable portion; and wherein information on force applied to the elongated medical device is calculated based on the information on the acceleration of the sub-movable portion.

According to a third aspect of the present disclosure, a force information calculation method for calculating information on force applied to an elongated medical device is disclosed, the method includes a step of acquiring target acceleration information on the elongated medical device, a step of driving the elongated medical device based on the target acceleration information on the elongated medical device, a step of acquiring actual acceleration information on the elongated medical device, and a step of calculating the information on the force applied to the elongated medical device from a difference between the actual acceleration information and the target acceleration information.

According to the present disclosure, a medical device drive apparatus and a force information calculation method capable of accurately detecting changes in force generated in a blood vessel are disclosed.

BRIEF DESCRIPTION OF THE DRAWINGS

FIG. 10 is a schematic flowchart illustrating a process of acquiring "main movable portion acceleration information" which is information on acceleration of a main movable portion.

FIG. 11 is a schematic flowchart illustrating a process of acquiring "fine movable portion relative acceleration information" which is information on relative acceleration of a fine movable portion with respect to a fine drive unit body.

FIG. 12 is a schematic flowchart illustrating a main operation example of a guide wire drive apparatus system including the guide wire drive apparatus in FIG. 1.

FIG. 13 is another schematic flowchart illustrating a main operation example of the guide wire drive apparatus system including the guide wire drive apparatus in FIG. 1.

DETAILED DESCRIPTION

Hereinafter, preferred embodiments of the present disclosure will be described in detail with reference to the accompanying drawings.

Since the embodiments described below are preferred specific examples of the present disclosure, various technically preferable limitations are given. However, the scope of the present disclosure is not limited to these embodiments unless otherwise specified in the following description.

Figure 1:
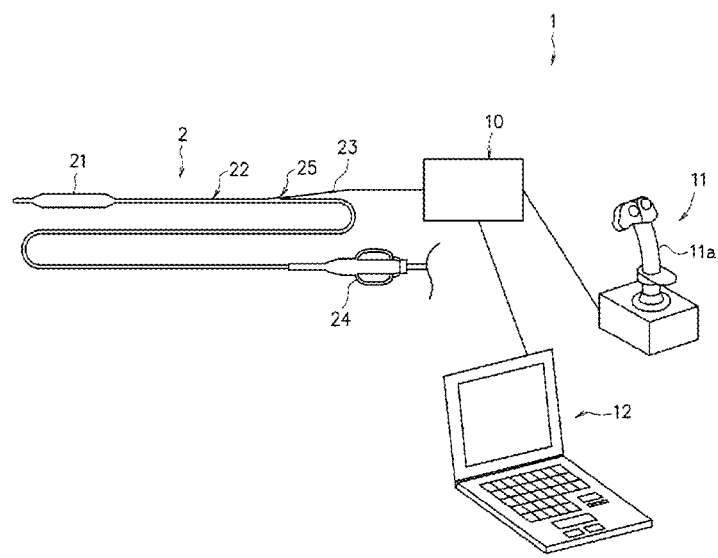
FIG. 1 is a schematic diagram illustrating an apparatus for a medical device such as a guide wire drive system including a medical device drive apparatus of the present disclosure such as a guide wire drive apparatus.

FIG. 1 is a schematic diagram illustrating an apparatus for a medical device such as a guide wire drive system 1 including a medical device drive apparatus of the present disclosure such as a guide wire drive apparatus 10.

As illustrated in FIG. 1, the guide wire drive system 1 has a balloon catheter 2 for insertion and disposal in a blood vessel of a living body of a patient, for example.

The balloon catheter 2 has a balloon 21 that inflates by injection of a contrast agent is disposed at the distal end of the balloon catheter 2.

Specifically, the balloon 21 is inflated at a stenosed site (lesion area) in the blood vessel of a patient to widen the stenosed site and treat the stenosed site.

The balloon catheter 2 of the present embodiment can be, for example, a balloon catheter for inflation of percutaneous transluminal coronary angioplasty (PTCA) used to widen the stenosed site of the coronary artery.

For example, the balloon catheter 2 of the present embodiment can be a balloon catheter used for the purpose of treatment and amelioration of the stenosed site formed inside a biological organ such as other blood vessels, the bile duct, the trachea, the esophagus, other alimentary canals, the urethra, an aurinasal lumen, and other internal organs.

As illustrated in FIG. 1, the balloon catheter 2 has an elongated shaft 22 having a flexibility that can be inserted into a living body lumen, and the balloon 21 that can be inflated and deflated is disposed at the distal end of the shaft 22.

A hub 24 for connecting the balloon catheter 2 to another device is disposed on the proximal side of the shaft 22.

The shaft 22 is also formed with an opening portion 25 through which, for example, a guide wire 23, which is an elongated medical device, can be led out.

The guide wire 23 is inserted into the blood vessel before the balloon 21 and has a structure for guiding the subsequent balloon 21 to the lesion area.

Therefore, the guide wire 23 is inserted from the opening portion 25 in FIG. 1 and disposed so as to penetrate from the distal end of the balloon 21.

In the present embodiment, as illustrated in FIG. 1, the guide wire drive apparatus 10 plays a role of inserting the guide wire 23 into the blood vessel of a patient.

Specifically, the guide wire 23 inserted into the blood vessel of a patient can be imaged by an X-ray imaging device (not illustrated), and the image can be displayed on a display 12 in FIG. 1.

In accordance with an exemplary embodiment, the drive of the guide wire drive apparatus 10 can be controlled by a doctor or the like who is an operator moving (swinging) a handle 11a, which is an example of an operation unit of a "joystick 11" which is an example of an input unit illustrated in FIG. 1, so as to tilt.

Therefore, the doctor or the like can insert the guide wire 23 into the blood vessel of a patient by operating the handle 11a of the joystick 11 away from the patient while visually confirming the display 12.

Thereby, the doctor or the like can avoid exposure by X-rays.

Figure 2:
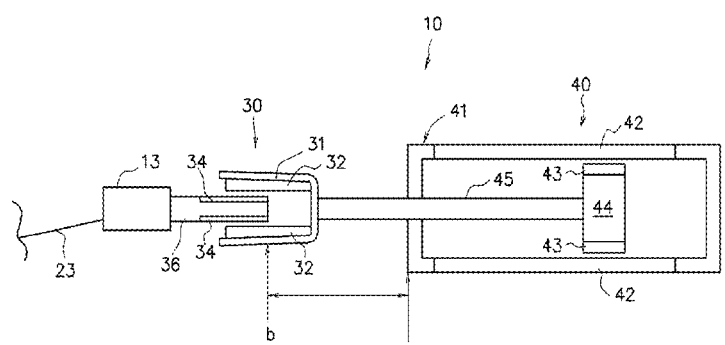
FIG. 2 is a schematic diagram illustrating main mechanical configuration of the guide wire drive apparatus in FIG. 1.

FIG. 2 is a schematic diagram illustrating main mechanical configuration of the guide wire drive apparatus 10 in FIG. 1.

As illustrated in FIG. 2, the guide wire drive apparatus 10 has, for example, a wire attachment portion 13 that is a support portion to which the guide wire 23 in FIG. 1 is attached.

In accordance with an exemplary embodiment, the wire attachment portion 13 can then be connected to a fine drive unit which is an example of a sub-drive unit. Specifically, the wire attachment portion 13 can be connected to, for example, a fine movable portion 36 of a voice coil motor (VCM) 30 which is a fine drive unit.

In accordance with an exemplary embodiment, the fine movable portion 36 is an example of a sub-movable portion.

The voice coil motor (VCM) 30 is a motor that converts electrical energy into kinetic energy using a magnetic field as a medium, and, in the present embodiment, can be, for example, a type in which a coil moves in a magnetic field.

In accordance with an exemplary embodiment, the VCM 30 can reduce the weight of the fine movable portion 36 and is a motor capable of performing precise control since it has relatively excellent electrical response, can move at high speed, and can generate thrust almost proportional to the current.

Therefore, in the present embodiment, the VCM 30 in FIG. 2 can detect relatively minute force with respect to the guide wire 23 in the blood vessel, for example, external force (such as reaction force) with high accuracy.

Specifically, the VCM 30 has the following configuration.

Figure 3:
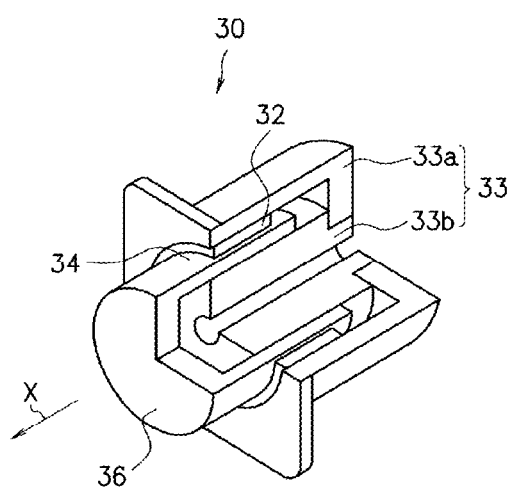
FIG. 3 is a schematic diagram illustrating a voice control motor (VCM) in FIG. 2 in a three-dimensional manner.

FIG. 3 is a schematic diagram illustrating the VCM 30 in FIG. 2 in a three-dimensional manner.

As illustrated in FIGS. 2 and 3, the VCM 30 can include a fine drive unit body (housing) 33 which is a sub-drive unit body, and the fine drive unit body 33 has an outer yoke 33*a* and an inner yoke 33*b*.

A magnet 32 is disposed inside the outer yoke 33*a*.

A coil 34 is disposed opposite to the magnet 32, and the coil 34 is formed in the fine movable portion 36.

As illustrated in FIG. 2, the wire attachment portion 13 can be connected to the fine movable portion 36.

In accordance with an exemplary embodiment, when the VCM 30 is energized, the fine movable portion 36 moves relative to the fine drive unit body 33 due to a change in the magnetic field of the fine drive unit body 33, and moves in the direction of the distal end of an arrow X in FIG. 3, for example.

When the guide wire 23, for example, attaches to the blood vessel wall and a force is applied to the VCM 30 and the force exceeds the force that the fine movable portion 36 moves from the fine drive unit body 33 to the distal end of the arrow X in FIG. 3, conversely, the fine movable portion 36 moves in a proximal direction of the arrow X in FIG. 3.

Therefore, in the present embodiment, the VCM 30 allows the fine movement of the guide wire 23, and when force is applied to the guide wire 23, the fine movable portion 36 moves by reacting precisely even if the force is relatively small.

In accordance with an exemplary embodiment, since the fine movable portion 36 of the VCM 30 in the present embodiment need to respond to the force on the guide wire 23 with relative high accuracy, the current can be adjusted so as to be disposed at a predetermined position.

For example, control can be performed such that the reference part of the fine movable portion 36 (reference portion), such as the proximal side of the fine movable portion 36 is located at a reference point (b) of the fine drive unit body 33 illustrated in FIG. 2, or is located within a predetermined range of the reference point (b) (for example, a predetermined range in the moving direction of the fine movable portion 36 in FIG. 2).

As illustrated in FIG. 2, the guide wire drive apparatus 10 can include, for example, a linear motor 40, which is a main drive unit.

As illustrated in FIG. 2, the linear motor 40 can include a main drive unit body (housing) 41, and magnets 42 arranged in a straight line are arranged in the main drive unit body 41.

A coil 43 disposed so as to face the magnet 42 is disposed on a main movable portion 44 side.

In accordance with an exemplary embodiment, the main movable portion 44 can be configured to move along the magnet 42 when energized.

As illustrated in FIG. 2, an attachment shaft 45 is connected to the main movable portion 44, and the fine drive unit body 33 of the VCM 30 is connected to the distal side of the attachment shaft 45.

In accordance with an exemplary embodiment, the main movable portion 44 is connected to the fine drive unit body 33 via the attachment shaft 45, and when the linear motor 40 is driven and the main movable portion 44 moves toward the distal side in FIG. 2, the VCM 30 also moves to the distal side (the guide wire 23 side).

In the present embodiment, the linear motor 40 can be used for a relatively long movement of the guide wire 23, which can be difficult with the VCM 30, for example, when the guide wire 23 is inserted into a blood vessel and the guide wire 23 is advanced to a target site.

In accordance with an exemplary embodiment, the VCM 30 can then be used when measuring relatively minute force from the blood vessel in a target site.

In particular, for example, since the guide wire 23 is connected to the fine movable portion 36 of the VCM 30 via the wire attachment portion 13, the VCM 30 can be configured to rather easily detect minute force or the like from the guide wire 23.

In accordance with an exemplary embodiment, for example, the linear motor 40 takes charge of the large force of moving the elongated guide wire 23 over relatively long distances, and the VCM 30, for example, takes charge of the detection of information on minute force applied to the elongated guide wire 23 since it can be difficult to detect with the linear motor 40, the above-described conflicting demands can be achieved at the same time.

In accordance with an exemplary embodiment, the guide wire drive apparatus 10 illustrated in FIG. 1 includes a central processing unit (CPU), a random access memory (RAM), and a read only memory (ROM), and the CPU, the RAM, the ROM can be connected via a bus.

Figure 4:
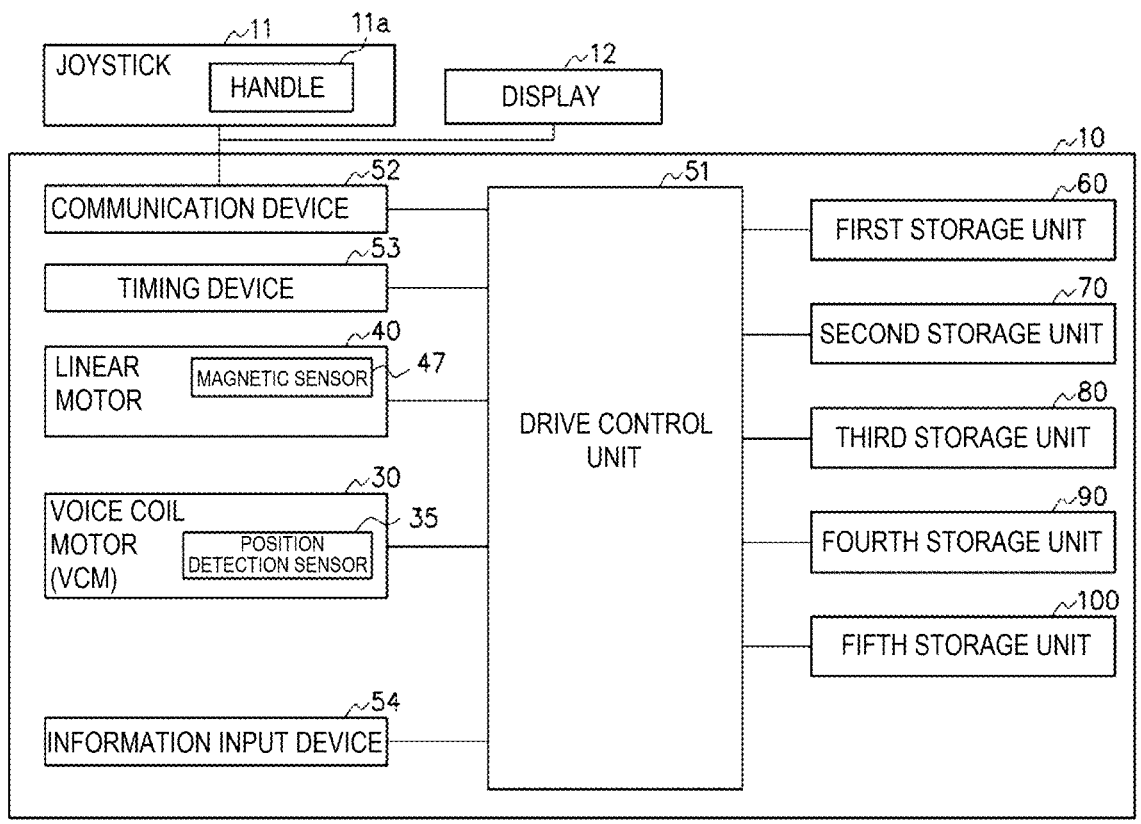
FIG. 4 is a schematic block diagram illustrating a main configuration of the guide wire drive apparatus in FIG. 1.

FIG. 4 is a schematic block diagram illustrating a main configuration of the guide wire drive apparatus 10 in FIG. 1.

As illustrated in FIG. 4, the guide wire drive apparatus 10 can include a drive control unit 51, the drive control unit 51 controls a communication device 52, a timing device 53, an information input device 54, the linear motor 40, and the VCM 30 illustrated in FIG. 2 for communicating with the joystick 11 and the display 12.

In accordance with an exemplary embodiment, the drive control unit 51 controls a first storage unit 60, a second storage unit 70, a third storage unit 80, a fourth storage unit 90, and a fifth storage unit 100 as illustrated in FIG. 4.

FIG. 5 through FIG. 9 are schematic block diagrams illustrating configurations of the first storage unit 60, the second storage unit 70, the third storage unit 80, the fourth storage unit 90, and the fifth storage unit 100. These contents will be described later.

As illustrated in FIG. 4, in the coil 43 part of the main movable portion 44 of the linear motor 40, a magnetic sensor 47, which is a first position sensor, is disposed, and can be used when acquiring the information on absolute position (i.e., position relative to the reference (non-moving) housing) of the main movable portion 44 as described later.

In the VCM 30, for example, a position detection sensor 35, which is a second position sensor that detects the position of the fine movable portion 36 via the Hall element is formed, and as described later, can be used when the information on relative position of the fine movable portion 36 with respect to the fine drive unit body 33 is acquired.

With this relative position information, it can be possible to determine whether the proximal side which is the reference of the fine movable portion 36 in FIG. 2 is coincident with the reference point (b) of the fine drive unit body 33, or is disposed within a predetermined range of the reference point (b).

In accordance with an exemplary embodiment, in the present embodiment, the information on absolute position of the main movable portion 44 is acquired with the magnetic sensor 47, information on the speed of the main movable portion 44 is acquired based on the position information, and, the information on acceleration of the main movable portion 44 can be acquired from the speed information.

FIG. 10 is a schematic flowchart illustrating a process of acquiring main movable portion acceleration information which is information on acceleration of the main movable portion 44.

Hereinafter, the process of acquiring the main movable portion acceleration information on the main movable portion 44 will be described using the flowchart.

In step (hereinafter, referred to as ST) 1 in FIG. 10, a main movable portion position acquisition unit (program) 61 in FIG. 5 operates, the movement of the main movable portion 44 of the linear motor 40 is detected by a signal from the magnetic sensor 47, and the information on position of the main movable portion 44 is grasped.

Figure 6:
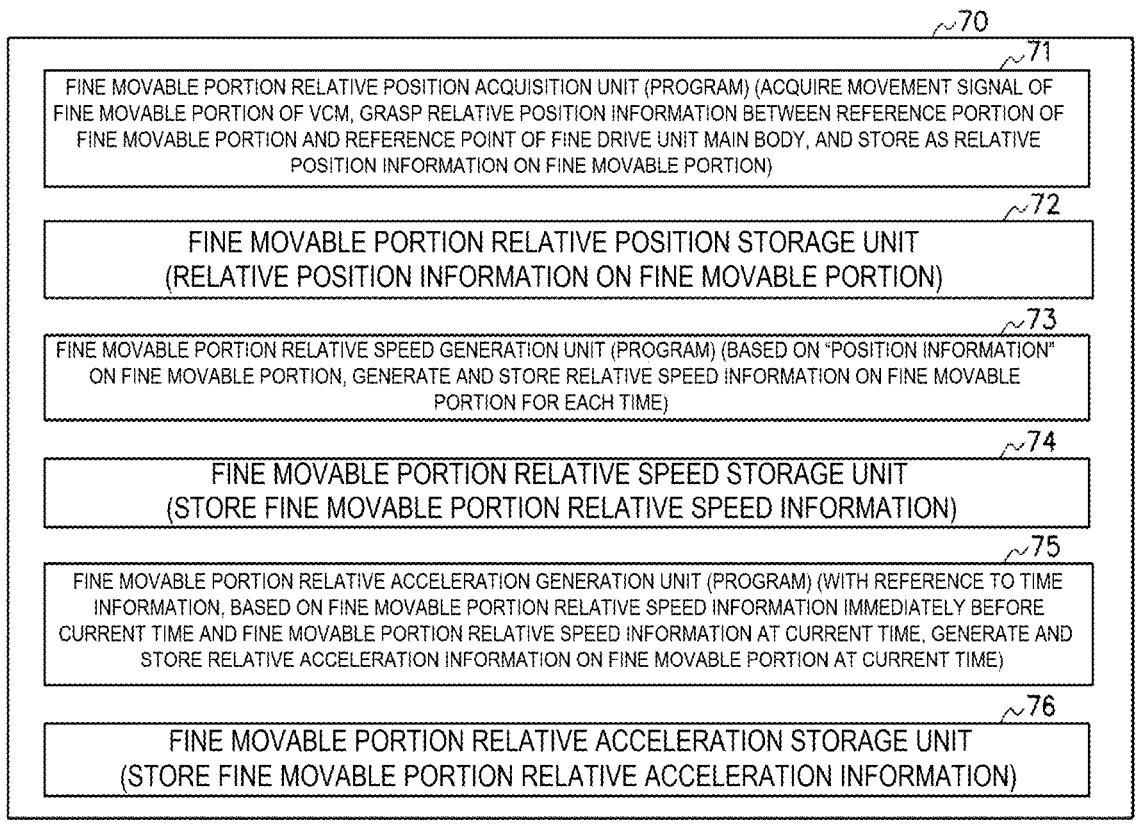
FIG. 6 is a schematic block diagram illustrating a main configuration of a second storage unit.

In accordance with an exemplary embodiment, the information on position of the main movable portion 44 is stored in a main movable portion position storage unit 62 in FIG. 6 as the information on position of the main movable portion 44.

Thereby, the position information on the movement of the main movable portion 44 in FIG. 2 can be acquired.

Next, the process proceeds to ST2. In ST2, the information on speed of the main movable portion 44 is generated.

Figure 5:
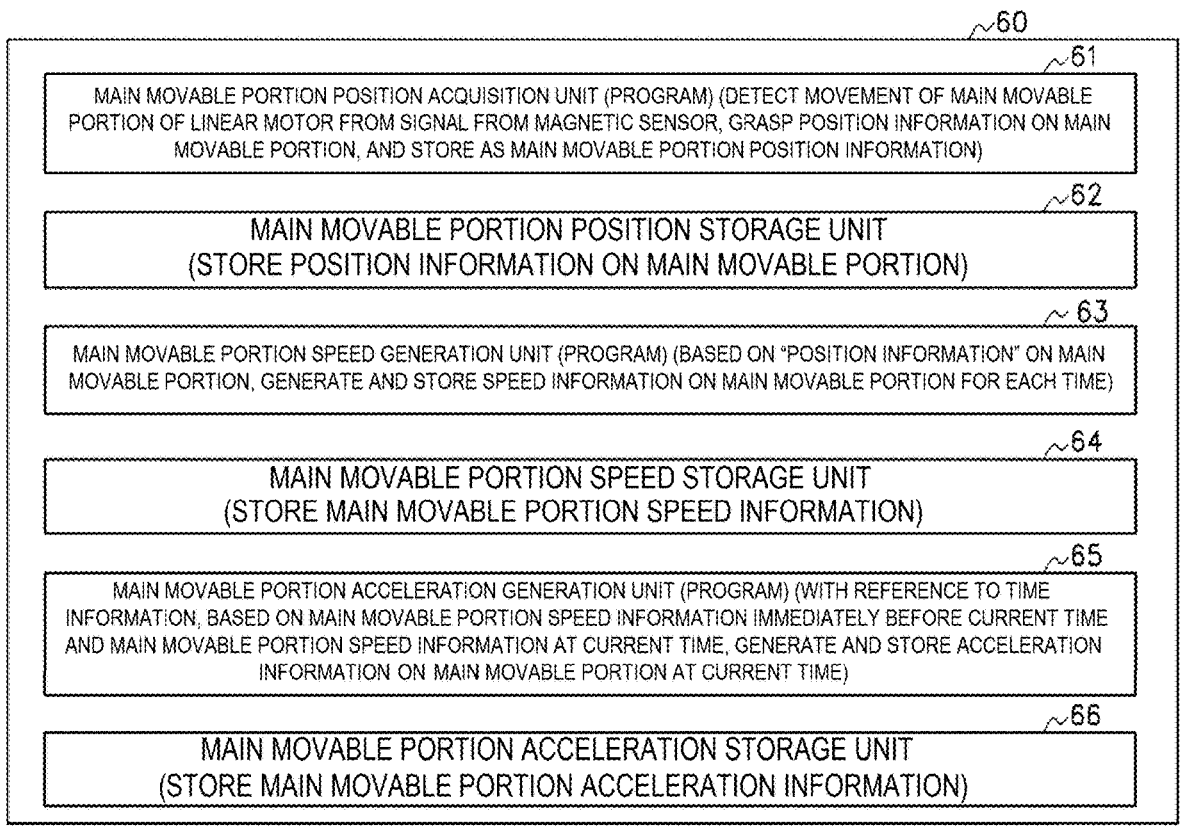
FIG. 5 is a schematic block diagram illustrating a main configuration of a first storage unit.

In accordance with an exemplary embodiment, a main movable portion speed generation unit (program) 63 in FIG. 5 operates, and based on the position information of the main movable portion 44 in the main movable portion position storage unit 62 in FIG. 5, main movable portion speed information which is the information on speed of the main movable portion 44 for each time is generated and stored in a main movable portion speed storage unit 64 in FIG. 5.

In accordance with an exemplary embodiment, based on the position information and the time information, the speed information of the main movable portion 44 is generated and stored.

Next, the process proceeds to ST3. In ST3, the information on acceleration of the main movable portion 44 is generated.

In accordance with an exemplary embodiment, a main movable portion acceleration generation unit (program) 65 in FIG. 5 operates with reference to the main movable portion speed storage unit 64 in FIG. 5.

With reference to the time information, based on the main movable portion speed information immediately before the current time and the main movable portion speed information at the current time, main movable portion acceleration information which is the information on acceleration of the main movable portion 44 at the current time is generated and stored in a main movable portion acceleration storage unit 66 in FIG. 5.

In the present embodiment, the acceleration information of the main movable portion 44 of the linear motor 40 in FIG. 2 can be acquired in this way.

In the present embodiment, the information on relative position of the fine movable portion 36 with respect to the fine drive unit body 33 is acquired with the position detection sensor 35, based on this relative position information, the information on relative speed of the fine movable portion 36 is acquired, and the information on relative acceleration of the fine movable portion 36 is acquired from the relative speed information.

FIG. 11 is a schematic flowchart illustrating a process of acquiring the fine movable portion relative acceleration information which is the information on relative acceleration of the fine movable portion 36 with respect to the fine drive unit body 33.

Hereinafter, using the same flowchart, a process of acquiring the fine movable portion relative acceleration information of the fine movable portion 36 with respect to the fine drive unit body 33 will be described.

First, in ST11, a fine movable portion relative position acquisition unit (program) 71 in FIG. 6 operates, and the movement of the fine movable portion 36 of the VCM 30 is acquired by the position detection sensor 35.

Then, the reference part of the fine movable portion 36 (reference portion), for example, the information on relative position of the proximal side of the fine movable portion 36 and the reference point (b) of the fine drive unit body 33 is grasped.

Then, the information on relative position of the proximal side of the fine movable portion 36 and the reference point (b) of the fine drive unit body 33 is stored in a fine movable portion relative position storage unit 72 in FIG. 6 as information on relative position of the fine movable portion 36.

Next, the process proceeds to ST12. In ST12, a fine movable portion relative speed generation unit (program) 73 in FIG. 6 operates, and based on the position information of the fine movable portion 36 in the fine movable portion relative position storage unit 72 in FIG. 6, the fine movable portion relative speed information which is the information on relative speed of the fine movable portion for each time is generated and stored in a fine movable portion relative speed storage unit 74 in FIG. 6.

In accordance with an exemplary embodiment, based on the relative position on the fine movable portion 36 with respect to the fine drive unit body 33 and the time information, the relative speed of the fine movable portion 36 with respect to the fine drive unit body 33 is generated and stored.

Next, the process proceeds to ST13. In ST13, the information on relative acceleration of the fine movable portion 36 with respect to the fine drive unit body 33 can be generated.

In accordance with an exemplary embodiment, a fine movable portion relative acceleration generation unit (program) 75 in FIG. 6 operates with reference to the fine movable portion relative speed storage unit 74 in FIG. 6.

With reference to the time information, based on the fine movable portion relative speed information immediately before the current time and the fine movable portion relative speed information at the current time, fine movable portion relative acceleration information which is the information on relative acceleration of the fine movable portion 36 at the current time is generated and stored in a fine movable portion relative acceleration storage unit 76 in FIG. 6.

In the present embodiment, relative acceleration information of the fine movable portion 36 of the VCM 30 in FIG. 2 with respect to the fine drive unit body 33 can be acquired in this way.

FIGS. 12 and 13 are schematic flowcharts illustrating a main operation example of the guide wire drive system 1 including the guide wire drive apparatus 10 in FIG. 1.

The following description will be made along these flowcharts, and configurations of FIGS. 1 to 9 will be described.

First, in ST21 of FIG. 12, an operator such as a doctor starts the operation of the guide wire drive apparatus 10 of the guide wire drive system 1 in FIG. 1.

In accordance with an exemplary embodiment, the operator inserts the guide wire 23 into the blood vessel prior to the catheter.

At this time, the operator operates the guide wire 23 while irradiating a patient with an X-ray by an X-ray imaging device (not illustrated) and displaying the site on the display 12 by X-ray fluoroscopy.

Therefore, the operator can start the operation of the guide wire drive apparatus 10 while avoiding exposure to X-rays.

Next, the process proceeds to ST22. In ST22, the operator operates the guide wire drive apparatus 10 by tilting the handle 11a of the joystick 11 in FIG. 1.

The target acceleration in the movement of the guide wire 23 in FIG. 1 is determined by the degree of inclination of the handle 11a.

Figure 7:
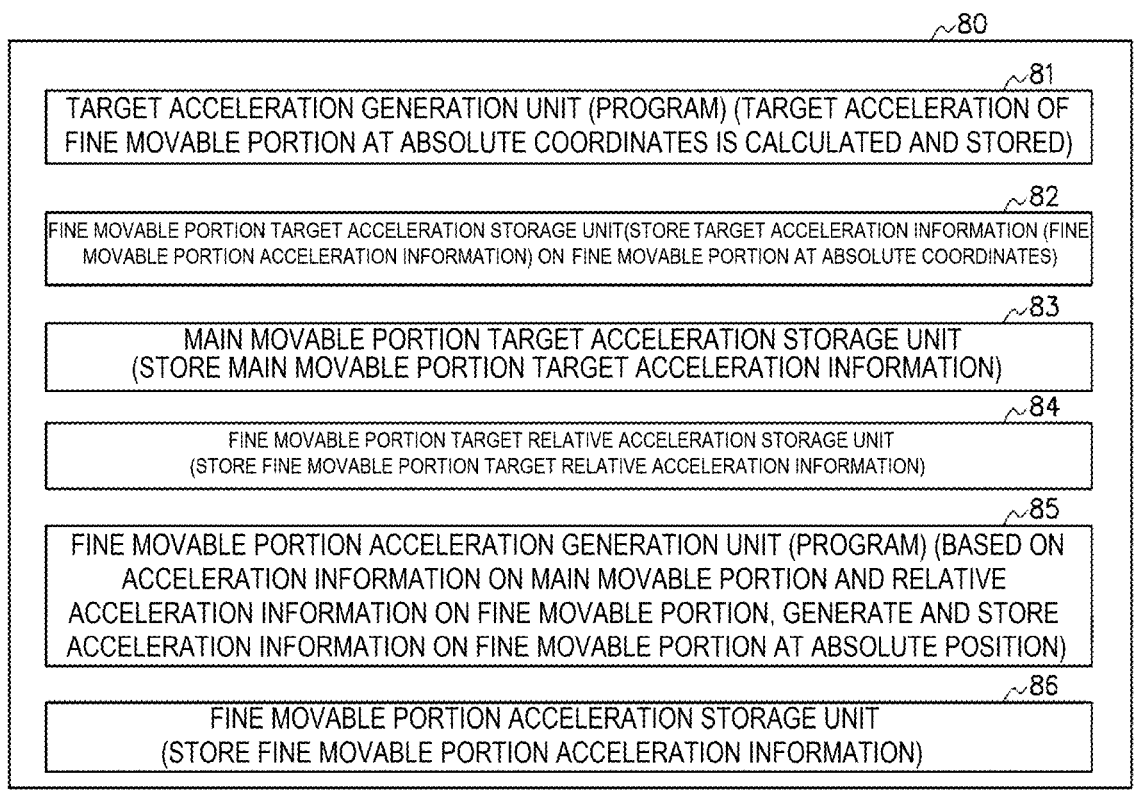
FIG. 7 is a schematic block diagram illustrating a main configuration of a third storage unit.

In accordance with an exemplary embodiment, a target acceleration generation unit (program) 81 in FIG. 7 operates, and the target acceleration at absolute coordinates (position) of the fine movable portion 36 is calculated from the target acceleration of the guide wire 23 and stored in a fine movable portion target acceleration storage unit 82 in FIG. 7.

Here, the target acceleration of the fine movable portion 36 at the absolute coordinates (position) indicates the acceleration on the distal side (the wire attachment portion 13 side) of the fine movable portion 36 in FIG. 2 at the absolute coordinates (position).

Therefore, the acceleration related to the movement of the guide wire 23 connected to the fine movable portion 36 via the wire attachment portion 13 is controlled by the acceleration of the fine movable portion 36 at the absolute coordinates (position).

In the present embodiment, the target acceleration of the fine movable portion 36 at the absolute coordinates (position) is calculated from the target acceleration of the guide wire 23. However, the present disclosure is not limited to this, and the target acceleration of the guide wire 23 may be the target acceleration of the fine movable portion 36 at the absolute coordinates (position).

Next, the process proceeds to ST23. In ST23, the relative position information between the reference portion (the proximal side of the fine movable portion 36) of the fine movable portion 36 and the reference point (b) of the fine drive unit body 33 is acquired.

That is, deviation information between the reference portion of the fine movable portion 36 and the reference point (b) of the fine drive unit body 33 is acquired.

Next, in ST24, from the target acceleration information on the fine movable portion 36 at the absolute position stored in the fine movable portion target acceleration storage unit 82 in FIG. 7, main movable portion target acceleration which is the target acceleration of the main movable portion 44 at the absolute position and fine movable portion target relative acceleration which is the target relative acceleration of the fine movable portion 36 with respect to the fine drive unit body 33 are determined.

Then, these main movable portion target acceleration and fine movable portion target relative acceleration can be stored in a main movable portion target acceleration storage unit 83 and a fine movable portion target relative acceleration storage unit 84 in FIG. 7, respectively.

In making this determination, when the reference portion of the fine movable portion 36 is deviated from the reference point (b) of the fine drive unit body 33, the distribution ratio to the main movable portion target acceleration and fine movable portion target relative acceleration is adjusted so as to cancel the deviation.

Next, the process proceeds to ST25 and ST26 in FIG. 12.

In ST25, the main movable portion 44 in FIG. 2 calculates the force (electric power) to become the main movable portion target acceleration information of the main movable portion target acceleration storage unit 83 in FIG. 7 and supplies the electric power to the linear motor 40.

Thereby, the linear motor 40 is driven, and the main movable portion 44 moves relative to the main drive unit body 41.

In ST26, the fine movable portion 36 calculates the force (electric power) to become fine movable portion target relative acceleration information of the fine movable portion target relative acceleration storage unit 84 in FIG. 6 and supplies the electric power to the VCM 30.

Thereby, the VCM 30 is driven, and the fine movable portion 36 moves relative to the fine drive unit body 33.

The process proceeds to ST27 after ST25 and proceeds to ST27 after ST26. In accordance with an exemplary embodiment, ST25 and ST26 may be executed simultaneously.

In ST27, the main movable portion acceleration information immediately before applying the force (electric power) to become the main movable portion target acceleration with respect to the linear motor 40 is acquired from the main movable portion acceleration storage unit 66 in FIG. 5 and stored.

In ST28, the fine movable portion relative acceleration information immediately before applying the force (electric power) to become fine movable portion target relative acceleration with respect to the VCM 30 is acquired from the fine movable portion relative acceleration storage unit 76 in FIG. 6 and stored.

In accordance with an exemplary embodiment, since the information on acceleration of the main movable portion 44 of the linear motor 40 in FIG. 2 and the information on relative acceleration of the fine drive unit body 33 of the VCM 30 with respect to the fine movable portion 36 can be acquired, in the following processes, the information on acceleration of the fine movable portion 36 at the absolute position is generated, and the information on acceleration of the guide wire 23 is estimated.

That is, in ST29, a fine movable portion acceleration generation unit (program) 85 in FIG. 7 operates with reference to the main movable portion acceleration storage unit 66 in FIG. 5 and the fine movable portion relative acceleration storage unit 76 in FIG. 6.

Then, based on the information on acceleration of the main movable portion 44 and the information on relative acceleration of the fine movable portion 36 with respect to the fine drive unit body 33, fine movable portion acceleration information which is information on acceleration of the fine movable portion at the absolute position is generated and stored in a fine movable portion acceleration storage unit 86 in FIG. 7.

In accordance with an exemplary embodiment, as illustrated in FIG. 2, the acceleration of the guide wire 23 is estimated from the acceleration of the fine movable portion 36 at the absolute position, and the acceleration of the fine movable portion 36 at the absolute position is obtained from the acceleration of the main movable portion 44 of the linear motor 40 and the relative acceleration of the fine movable portion 36 of the VCM 30 with respect to the fine drive unit body 33.

For this reason, in this process, this calculation is executed, and the acceleration information (fine movable portion acceleration information) of the fine movable portion 36 at the absolute position is acquired.

Thus, in the present embodiment, since the acceleration information can be obtained without disposing, for example, a separate position sensor for using the information on absolute position of the wire attachment portion 13 to which the guide wire 23 is connected, the cost can be reduced.

In the present embodiment, the acceleration of the fine movable portion 36 at the absolute position is acquired from the acceleration of the main movable portion 44 of the linear motor 40 and the relative acceleration on the fine movable portion 36 of the VCM 30. However, the present disclosure is not limited to this, and a position sensor that acquires the information on absolute position of the fine movable portion 36 may be disposed separately.

In accordance with an exemplary embodiment, the position sensor may detect an end portion of the fine movable portion 36, or may detect a position of the end portion of the wire attachment portion 13 connected to the fine movable portion 36.

In accordance with an exemplary embodiment, based on such absolute position information detected by a separate position sensor, the information on acceleration of the fine movable portion 36 or the wire attachment portion 13 may be obtained, and this may be used as the acceleration of the guide wire 23.

In this case, relatively highly accurate acceleration information can be acquired.

In the present embodiment, the positions of the main movable portion 44 and the fine movable portion 36 can be detected by the magnetic sensor 47 and the position detection sensor 35, respectively, and the speed and acceleration are obtained. However, the present disclosure is not limited to this, and a speed sensor or an acceleration sensor may be used instead of the position detection sensor 35 and the magnetic sensor 47.

In the present embodiment, the acceleration of the fine movable portion 36 at the absolute position is obtained from the acceleration of the main movable portion 44 and the fine movable portion 36. However, the present disclosure is not limited to this, and a position sensor for detecting the absolute position of the fine movable portion 36, a speed sensor for detecting the speed, and an acceleration sensor for detecting the acceleration may be disposed, and the acceleration of the fine movable portion 36 at the absolute position may be obtained directly.

Next, the process proceeds to ST30. In ST30, the information on acceleration of the fine movable portion 36 at the absolute position acquired in ST29 is compared with the target acceleration information on the fine movable portion 36, and acceleration difference information is generated.

Figure 8:
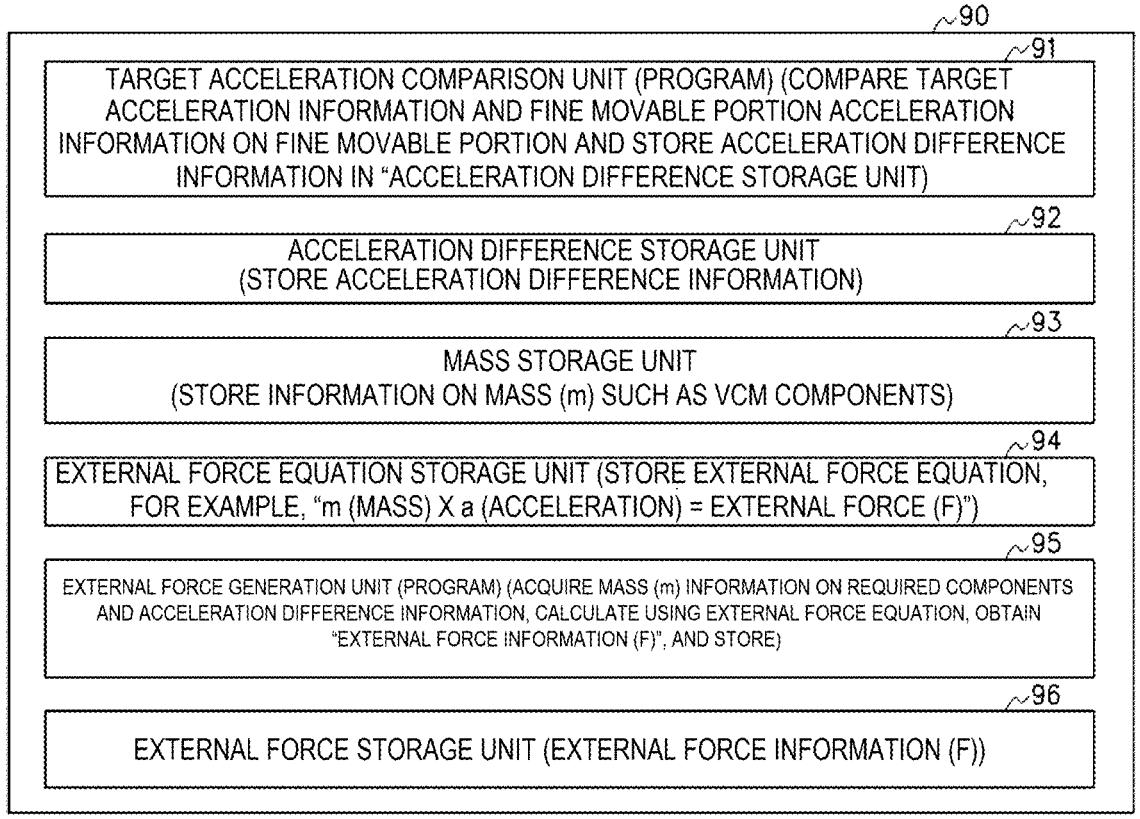
FIG. 8 is a schematic block diagram illustrating a main configuration of a fourth storage unit.

Specifically, a target acceleration comparison unit (program) 91 in FIG. 8 operates, the target acceleration information on the fine movable portion 36 in the fine movable portion target acceleration storage unit 82 in FIG. 7 at the absolute position is compared with the fine movable portion acceleration information on the fine movable portion acceleration storage unit 86 in FIG. 7, and the acceleration difference information is generated and stored in an acceleration difference storage unit 92 in FIG. 8.

In the present embodiment, the fine movable portion acceleration information is generated from the main movable portion acceleration information and the fine movable portion relative acceleration information, the fine movable portion acceleration information is compared with the fine movable portion target acceleration information, and the acceleration difference information can be acquired. However, the present disclosure is not limited to this, and the main movable portion acceleration difference information generated by comparing the main movable portion acceleration information with the main movable portion target acceleration information and the fine movable portion relative acceleration difference information generated by comparing the fine movable portion relative acceleration information with the fine movable portion target relative acceleration information may be added together.

That is, when the fine movable portion acceleration information is smaller than the fine movable portion target acceleration information, a relatively minute (or relatively small) force is applied to the guide wire 23 from, for example, a blood vessel, so that some abnormality may occur.

In accordance with an exemplary embodiment, when the fine movable portion acceleration information is larger than the fine movable portion target acceleration information, a force that pulls the guide wire 23 to the blood vessel is working, so that some abnormality may occur in the same manner.

Therefore, in the present embodiment, the external force is obtained in the following processes without using a force sensor.

Specifically, the process proceeds to ST31. In ST31, an external force generation unit (program) 95 in FIG. 8 operates with reference to an external force equation storage unit 94 in FIG. 8.

In the external force equation storage unit 94, an equation for external force calculation, for example, m (mass)×a (acceleration)=external force (F) is stored.

In accordance with an exemplary embodiment, obtaining the force (F) by multiplying mass (m) by acceleration (a) is stored.

In the present process, information on the mass (m) of required components can be acquired from a mass storage unit 93 in FIG. 8, and the acceleration difference information can be acquired from acceleration difference storage unit 92 in FIG. 8.

Figure 9:
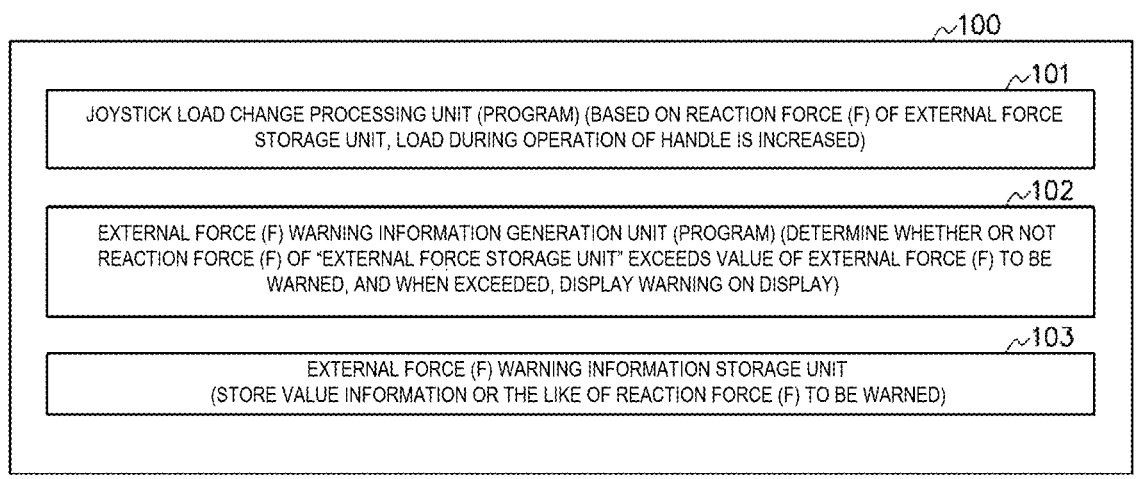
FIG. 9 is a schematic block diagram illustrating a main configuration of a fifth storage unit.

Then, the calculation is performed using the above-described equation, and the external force information (F) can be obtained and stored in an external force storage unit 96 in FIG. 9.

In accordance with an exemplary embodiment, the force (F) obtained in this way corresponds to the force (for example, applied force (external force)) exerted on the guide wire 23 from a blood vessel.

In this way, according to the present embodiment, the force (F) applied to the guide wire 23 in the blood vessel can be accurately grasped without specially disposing a force sensor for detecting the force.

In the present embodiment, since the force (F) is grasped by the movement of the fine movable portion 36 of the VCM 30, it is possible to detect an extremely minute (or extremely small) force change.

In the guide wire drive apparatus 10 of the guide wire drive system 1 of the present embodiment, when the guide wire 23 moves relatively long distance in the blood vessel, the guide wire 23 can be moved to the target position relatively quickly since the guide wire 23 can be moved by the linear motor 40 having a relatively large force.

In accordance with an exemplary embodiment, a fine external force applied to the guide wire 23 due to abnormality in the blood vessel can be detected by the movement of the fine movable portion 36 of the VCM 30 with relatively high accuracy.

Therefore, in the guide wire drive apparatus 10 of the present embodiment, the linear motor 40 takes charge of relatively large forces that move the elongated guide wire 23 over relatively long distances, and the fine movable portion 36 of the VCM 30, for example, takes charge of the detection of information on the minute force applied to the elongated guide wire 23 since detection can be difficult with the linear motor 40 so that the above-described conflicting demands can be achieved at the same time.

After calculating the external force (F) in ST31, the process proceeds to ST32. In ST32, a joystick load change processing unit (program) 101 in FIG. 9 operates, and based on the external force (F) of the external force storage unit 96 in FIG. 8, the load during the operation of the handle 11a can be increased.

In accordance with an exemplary embodiment, by increasing the load during the operation of the handle 11a as described above, the operator who operates the handle 11a can feel the force applied to the guide wire 23 from the blood vessel, the apparatus rather easily grasps the occurrence of abnormality.

Next, the process proceeds to ST33. In ST33, an external force (F) warning information generation unit (program) 102 in FIG. 9 operates, and refers to an external force (F) warning information storage unit 103 in FIG. 9.

In accordance with an exemplary embodiment, the external force (F) warning information storage unit 103 stores information on the value of external force (F) to be warned.

Therefore, in the present step (ST33), it is determined whether or not the external force (F) of the external force storage unit 96 in FIG. 8 exceeds the value of the external force (F) to be warned.

If the external force (F) is exceeded, a warning is display on the display 12 in ST34.

Thus, by displaying a "warning" on the display 12, the operator can be alerted.

In accordance with an exemplary embodiment, when the value of the external force (F) is equal to or greater than a predetermined value, the guide wire drive apparatus 10 may be forcibly stopped.

In this case, the guide wire drive apparatus 10 becomes relatively safer and more reliable.

Following ST34, if a stop signal is input at ST35, the same process is repeated.

The present disclosure is not limited to the above-described embodiment.

In the present embodiment, in ST33, it is determined whether or not to warn whether or not the predetermined value is exceeded. However, the present disclosure is not limited to this, and it may be determined whether the inclination of the external force (F) rose suddenly.

In the present embodiment, a warning is displayed in ST34. However, the present disclosure is not limited to this, and the guide wire drive apparatus 10, for example, may forcibly retract, for example, about 10 mm in the direction of extracting the guide wire 23 from the blood vessel.

Furthermore, in the present embodiment, an example is shown in which the control can be performed so that the reference of (proximal side) of the fine movable portion 36 of the VCM 30 is always maintained at the reference point (b) of the fine drive unit body 33. However, the present disclosure is not limited to this, and the position of the fine movable portion 36 of the VCM 30 may not be controlled until the guide wire 23 is brought close to the vicinity of the target site in the blood vessel by the linear motor 40 and may be controlled such that the reference (proximal side) of the fine movable portion 36 of the VCM 30 is maintained at the reference point (b) of the fine drive unit body 33 after being brought close to the vicinity of the target site.

In the present embodiment, an example in which the VCM 30 is used as a sub-drive unit is shown. However, the present disclosure is not limited to this, and a linear motion mechanism using a pneumatic cylinder or a linear motor in which the mass of the movable unit is reduced and the friction is reduced may also be used.

Furthermore, although the example which uses the linear motor 40 as a main drive unit is shown. However, the present disclosure is not limited to this, and a linear motion mechanism combining a feed screw and a motor may be used.

The detailed description above describes to a medical device drive apparatus and a force information calculation method for remote operation of a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device drive apparatus for inserting an elongated medical device into a blood vessel comprising:
    a main drive unit configured to enable movement of the elongated medical device;
    a sub-drive unit configured to enable linear movement of the elongated medical device at a shorter distance than the main drive unit, and includes a sub-drive unit body and a sub-movable portion movable with respect to the sub-drive unit body;
    a sensor configured to acquire information on acceleration of the sub-movable portion; and
    a processor configured to calculate information on force applied to the elongated medical device based on the information on the acceleration of the sub-movable portion.

2. The medical device drive apparatus according to claim 1, further comprising:
    an input unit configured to input target acceleration information on the elongated medical device; and
    wherein the processor is configured to:
        obtain target acceleration information on the sub-movable portion based on the target acceleration information on the elongated medical device input into the input unit; and
        calculate the information on the force applied to the elongated medical device from a difference between the target acceleration information on the sub-movable portion and actual acceleration information on the sub-movable portion.

3. The medical device drive apparatus according to claim 1,
    wherein the main drive unit includes a main drive unit body and a main movable portion movable with respect to the main drive unit body; and
    the sub-drive unit body is configured to move with the movement of the main movable portion.

4. The medical device drive apparatus according to claim 3, wherein the sensor includes a first sensor configured to acquire information on acceleration of the main movable portion and a second sensor configured to acquire information on relative acceleration of the sub-movable portion with respect to the sub-drive unit body; and wherein the processor is configured to calculate the information on acceleration of the sub-movable portion based on the information on acceleration of the main movable portion and the information on relative acceleration of the sub-movable portion.

5. The medical device drive apparatus according to claim 4, wherein the first sensor is a first position sensor configured to acquire information on absolute position of the main movable portion;

the second sensor is a second position sensor configured to acquire information on relative position of the sub-movable portion with respect to the sub-drive unit body; and the processor is configured to:

calculate information on acceleration of the main movable portion from the information on absolute position of the main movable portion; and calculate the information on relative acceleration of the sub-movable portion from the information on relative position of the sub-movable portion.

6. The medical device drive apparatus according to claim 5, further comprising:

an input unit configured to input target acceleration information on the elongated medical device; and wherein the processor is configured to:

calculate target acceleration information on the sub-movable portion based on the target acceleration information on the elongated medical device input to the input unit; and determine target acceleration information on the main movable portion and target relative acceleration information on the sub-movable portion with respect to the sub-drive unit body based on the target acceleration information on the sub-movable portion.

7. The medical device drive apparatus according to claim 6, wherein, in the determination of the target acceleration information, the processor is configured to determine the target acceleration information on the main movable portion and the target relative acceleration information on the sub-movable portion so that a relative position of the sub-movable portion with respect to the sub-drive unit body is within a predetermined range.

8. The medical device drive apparatus according to claim 6, wherein processor is configured to:

calculate the information on the force applied to the elongated medical device based on a difference between the target relative acceleration information on the sub-movable portion and the information on relative acceleration of the sub-movable portion, and a difference between the target acceleration information on the main movable portion and the information on acceleration of the main movable portion.

9. The medical device drive apparatus according to claim 3, further comprising:

a handle of a joystick, the handle configured to input the target acceleration information on the elongated medical device to the joystick; and wherein the processor is configured to:

reflect the calculated information on the force applied to the elongated medical device by increasing a load on the handle of the joystick.

10. The medical device drive apparatus according to claim 1, wherein the processor is configured to:

generate a notification when the calculated information on the force applied to the elongated medical device exceeds a predetermined value.

11. The medical device drive apparatus according to claim 1, wherein the processor is configured to:

stop movement of the sub-movable portion when the calculated information on the force applied to the elongated medical device exceeds a predetermined value.

12. A medical device drive apparatus for inserting an elongated medical device into a blood vessel comprising:

a main drive unit configured to enable movement of the elongated medical device;

a sub-drive unit configured to enable linear movement of the elongated medical device, the sub-drive unit including a sub-drive unit body and a sub-movable portion movable with respect to the sub-drive unit body;

a sensor configured to acquire information on acceleration of the sub-movable portion; and a processor configured to calculate information on force applied to the elongated medical device based on the information on the acceleration of the sub-movable portion.

13. The medical device drive apparatus according to claim 12, further comprising:

an input unit configured to input target acceleration information on the elongated medical device; and wherein the processor is configured to:

obtain target acceleration information on the sub-movable portion based on the target acceleration information on the elongated medical device input into the input unit.

14. The medical device drive apparatus according to claim 13, wherein the processor is configured to:

calculate the information on the force applied to the elongated medical device from a difference between the target acceleration information on the sub-movable portion and actual acceleration information on the sub-movable portion.

15. The medical device drive apparatus according to claim 12, wherein the main drive unit includes a main drive unit body and a main movable portion movable with respect to the main drive unit body; and the sub-drive unit body is configured to move with the movement of the main movable portion.

16. The medical device drive apparatus according to claim 15, wherein the sensor includes a first sensor configured to acquire information on acceleration of the main movable portion and a second sensor configured to acquire information on relative acceleration of the sub-movable portion with respect to the sub-drive unit body; and wherein the processor is configured to:

calculate the information on acceleration of the sub-movable portion based on the information on acceleration of the main movable portion and the information on relative acceleration of the sub-movable portion.

17. The medical device drive apparatus according to claim 16, wherein the first sensor is a first position sensor configured to acquire information on absolute position of the main movable portion; and the second sensor is a second position sensor configured to acquire information on relative position of the sub-movable portion with respect to the sub-drive unit body.

18. The medical device drive apparatus according to claim 17, wherein the processor is configured to:

calculate the information on acceleration of the main movable portion from the information on absolute position of the main movable portion; and calculate the information on relative acceleration of the sub-movable portion from the information on relative position of the sub-movable portion.

19. A force information calculation method for calculating information on force applied to an elongated medical device with the medical device drive apparatus according to claim 1, the method comprising:

acquiring target acceleration information on the elongated medical device;

driving the elongated medical device based on the target acceleration information on the elongated medical device;

acquiring actual acceleration information on the elongated medical device; and calculating the information on the force applied to the elongated medical device from a difference between the actual acceleration information and the target acceleration information.

20. The method according to claim 19, further comprising:

giving a notification when the calculated information on the force applied to the elongated medical device exceeds a predetermined value.

* * * * *